(12) United States Patent
Glossop et al.

(10) Patent No.: US 10,429,347 B2
(45) Date of Patent: Oct. 1, 2019

(54) MEASUREMENT OF PARTICLE CHARGE

(71) Applicant: IZON SCIENCE LIMITED, Christchurch (NZ)

(72) Inventors: Benjamin Mark Glossop, Christchurch (NZ); Robert Vogel, Christchurch (NZ); Eva Weatherall, Christchurch (NZ); Martin David Jones, Christchurch (NZ)

(73) Assignee: IZON SCIENCE LIMITED, Christchurch (NZ)

( * ) Notice: Subject to any disclaimer, the term of this patent is extended or adjusted under 35 U.S.C. 154(b) by 612 days.

(21) Appl. No.: 14/916,405

(22) PCT Filed: Sep. 3, 2014

(86) PCT No.: PCT/GB2014/000347
§ 371 (c)(1),
(2) Date: Mar. 3, 2016

(87) PCT Pub. No.: WO2015/033090
PCT Pub. Date: Mar. 12, 2015

(65) Prior Publication Data
US 2016/0223492 A1    Aug. 4, 2016

(30) Foreign Application Priority Data

Sep. 3, 2013 (NZ) ........................ 615026

(51) Int. Cl.
*G01N 27/447* (2006.01)
*G01N 15/12* (2006.01)
(Continued)

(52) U.S. Cl.
CPC ....... *G01N 27/44791* (2013.01); *G01N 15/12* (2013.01); *G01N 15/1209* (2013.01);
(Continued)

(58) Field of Classification Search
CPC ......... G01N 27/44791; G01N 27/4163; G01N 27/44704; G01N 15/1209; G01N 15/12;
(Continued)

(56) References Cited

U.S. PATENT DOCUMENTS

| | | | |
|---|---|---|---|
| 2010/0021883 A1* | 1/2010 | Sowerby | B26F 1/00 435/6.11 |
| 2010/0025363 A1 | 2/2010 | Yamanaka et al. | |
| 2015/0060277 A1* | 3/2015 | Golovchenko | G01N 33/48721 204/453 |

FOREIGN PATENT DOCUMENTS

| | | |
|---|---|---|
| GB | 2493411 A | 2/2013 |
| WO | 2011/092218 A1 | 8/2011 |

(Continued)

OTHER PUBLICATIONS

Arjmandi et al. (N. Arjmandi, W.V. Roy, L. Lagae, G. Borghs, Measuring the electric charge and zeta potential of nanometer-sized objects using pyramidal-shaped nanopores, Analytical Chemistry 84 (2012) 8490-8496 (cited in IDS). (Year: 2012).*

(Continued)

*Primary Examiner* — Maris R Kessel
*Assistant Examiner* — Joshua L Allen
(74) *Attorney, Agent, or Firm* — Meunier Carlin & Curfman LLC

(57) ABSTRACT

A method of determining a charge of at least one test particle (as herein defined), comprising: applying one of an electric current or a voltage across an aperture connecting two chambers, whereby the chambers are at least partially filled with electrolyte and whereby the at least one test particle is suspended in the electrolyte of at least one of the chambers; measuring a value indicative of the other of the electric current or voltage across the aperture; determining a time interval between a first and a second point in time, the second point in time corresponding to a point in time when (Continued)

the measured current or voltage has reached a specific proportion of the measured current or voltage at the first point in time; and determining the charge of the at least one test particle by: determining a value indicative of an electrical velocity component of a total velocity of at least one calibration particle having a known charge, taking into account that the total velocity of the at least one calibration particle comprises a non zero-convective velocity component and the electrical velocity component; determining a value indicative of an electrical velocity component of a total velocity of the at least one test particle, taking into account that the total velocity of the at least one test particle comprises a non-zero convective-velocity component and the electrical velocity component; and using the determined values indicative of the electrical velocity components of the test particle and the calibration particle to calibrate the quantitative relationship between the charge of the at least one test particle and the determined time interval.

20 Claims, 8 Drawing Sheets

(51) Int. Cl.
G01N 27/416 (2006.01)
G01N 29/24 (2006.01)
G01N 15/10 (2006.01)
G01N 15/00 (2006.01)
G01R 29/24 (2006.01)

(52) U.S. Cl.
CPC ... G01N 27/4163 (2013.01); G01N 27/44704 (2013.01); G01R 29/24 (2013.01); *G01N 15/1218* (2013.01); *G01N 2015/0003* (2013.01); *G01N 2015/1075* (2013.01)

(58) Field of Classification Search
CPC ... G01N 2015/0003; G01N 2015/1075; G01N 15/1218; G01R 29/24
See application file for complete search history.

(56) References Cited

FOREIGN PATENT DOCUMENTS

WO    WO-2011092218 A1 * 8/2011 ............. G01N 15/12
WO    2013/017671 A1    2/2013

OTHER PUBLICATIONS

Kozak et al. (D Kozak, W Anderson, R Vogel, S Chen, F Antaw, M Trau, Simultaneous size and zeta-potential measurements of individual nanoparticles in dispersion using size-tunable pore sensors, ACS Nano, 6(8) (2012) 6990-6997; Cited in IDS). (Year: 2012).*
Arjmandi et al. (N Arjmandi, WV Roy, L Lagae, G Borghs, Measuring the electric charge and zeta potential of nanometer sized objects using pyramidal-shaped nanopores, Anal. Chem. 84 (2012) 8490-8496; Cited in IDS). (Year: 2012).*
Vogel et al. (R Vogel, W Anderson, J Eldridge, B Glossop, G Willmott, A variable pressure method for characterizing nanoparticle surface charge using pore sensors, Anal. Chem. 84 (2012) 3125-3131; Cited in IDS). (Year: 2012).*
First Office Action issued by the State Intellectual Property Office of the People's Republic of China in corresponding Chinese Application No. 201480048308.1, dated Dec. 4, 2017.
Arjmandi et al., "Measuring the Electric Charge and Zeta Potential of Nanometer-Sized Objects Using Pyramidal-Shaped Nanopores", Analytical Chemistry, 84, 20, pp. 1-31, 2012.
Arjmadni, N., et al., "Measuring the electric charge and zeta potential of nanometer-sized objects," Analytical Chemistry, ResearchGate, 2012, 84(20), 8490-8496.
Kozak, D., et al., "Simultaneous size and ζ-potential measurements of individual nanoparticles in dispersion using size-tunable pore sensors," ACS nano, 2012, 6(8), 6990-6997.
Vogel, R., et al., "A variable pressure method for characterizing nanoparticle surface charge using pore sensors," Analytical Chemistry, 2012, 84(7), 3125-3131.
International Search Report and Written Opinion of the International Searching Authority in Application No. PCT/GB2014/000347, dated Dec. 22, 2014, 9 pages.
International Preliminary Report on Patentability issued by the International Bureau of WIPO in Application No. PCT/GB2014/000347, dated Mar. 17, 2016, 7 pages.
Second Office Action issued by the State Intellectual Property Office of the People's Republic of China in corresponding Chinese Application No. 201480048308.1, dated Jun. 14, 2018.

* cited by examiner

MEASUREMENT OF PARTICLE CHARGE

FIELD OF THE INVENTION

The invention relates to a method for measuring the charge of particles, in particular the surface charge of nanometre to micron sized particles suspended in a fluid. The invention extends to apparatus for use in the above method, and to a computer program for use with such apparatus, for carrying out the above method.

BACKGROUND AND SUMMARY OF THE INVENTION

The surface charge of objects in the nanometre and micron range is a key factor in their stability and general reactivity. Surface charge and changes in surface charge can also be used to detect and quantify the presence of specific targets in a sample. The ability to accurately measure the surface charge of objects is therefore important for a range of users from industrial (e.g. paint, ink and coating manufacture) through to pharmaceutical (e.g. vaccine QA) and scientific research (e.g. developing nanomedicines and specific molecular diagnostic tests).

Current practice for measuring the surface charge of particles includes Dynamic Light Scattering (DLS) (Phase Analysis Light Scattering-Quasi Electric Light Scattering). Dynamic Light Scattering is used to measure particle and molecule size. This technique measures the diffusion of particles moving under Brownian motion, and converts this to size and a size distribution using the Stokes-Einstein relationship.

In conjunction with DLS Laser Doppler Micro-electrophoresis is used to measure the zeta potential or surface charge of particles. In this method an electric field is applied to a solution of molecules or a dispersion of particles, which then move with a velocity related to their zeta potential. This velocity is measured using a laser interferometric technique (Phase Analysis Light Scattering or PALS). This enables the calculation of electrophoretic mobility, and from this the zeta potential and zeta potential distribution.

However, the present inventors have appreciated that there are limitations to this approach. Due to the nature of the analysis individual particle sizes and zeta potentials are not measured, this is an "ensemble" technique. Separating similarly sized populations based on surface charge is therefore not possible; neither is identification of a subtle shift in surface charge of a group of particles, which could be used as a diagnostic measurement. The present inventors have appreciated that this limits the range of applications to which the technique may be applied.

A further limitation of DLS analysis, as appreciated by the present inventors, is that the average size distribution of a mixed population of particles is artificially skewed towards the larger particles, which scatter so much light that they can obscure smaller particles.

Another method used for the measurement of particle surface charge is Nanoparticle Tracking Analysis or NTA. NTA, like DLS, measures the Brownian motion of nanoparticles in 2 dimensions whose speed of motion, or diffusion coefficient, $D_t$, is related to particle size through the Stokes-Einstein equation. In NTA this motion is analysed by video; individual particle positional changes are tracked in two dimensions from which the particle diffusion is determined. Knowing $D_t$, the particle hydrodynamic diameter can be then determined on a particle by particle basis. By applying a bias voltage to the sample, NTA can also measure electrophoretic velocity and derive a zeta potential.

The present inventors have appreciated that limitations of NTA include the fact that a relatively small number of particles are analysed, and that it is possible to measure the same particle several times. Further, complex algorithms are applied to calculate the particle size and charge, and if the input settings are incorrect or not known the answer can be significantly erroneous. Additionally, compensation factors also need to be applied to balance both electro-osmotic flow and convection due to laser heating effects.

Another method used specifically for the measurement of particle surface charge is through the use of particle translation rate or duration as measured through Resistive Pulse Sensing.

Various techniques have been described to measure the relative electrophoretic velocity of populations of particles by adjusting either the voltage or the pressure applied across a nanopore and observing the change in either particle translocation rate or duration (typically FWHM) of the resistive pulses.

Vogel (Vogel, R., et al., "A Variable Pressure Method for Characterizing Nanoparticle Surface Charge Using Pore Sensors". *Analytical Chemistry*, 2012. 84(7): p. 3125-3131.) describes one such application where sample particles are placed on both sides of the nanopore, and the pressure applied across a nanopore is adjusted until the flow of particles reverses direction. The applied pressure required to reach this "inversion point" is used as a measure of electrophoretic mobility. At the inversion point, the time it takes for particles to translocate the pore tends towards infinity, so translocation duration can also be used as an indicator.

As appreciated by the present inventors, the main limitations of these methods are that they are ensemble methods (not particle by particle), and that they are time-consuming as they require the adjusting of many parameters and many measurements. Additionally, with the pressure-sweep method in particular, the, duration of the measurement and the reversal of the fluid flow greatly increase the chance of a particle partially blocking the sensing zone.

Another method for the measurement of surface particle charge is described by Kozak (Kozak, D., et al., "Simultaneous size and ζ-potential measurements of individual nanoparticles in dispersion using size-tunable pore sensors". *ACS nano*, 2012. 6(8): 6990-6997.). This method provides single particle charge measurements through analysing resistive pulse data. Kozak et al. describes a method for modelling a conical nanopore and calculating all of the forces on a particle passing through the nanopore. This method produces particle by particle surface charge data that can distinguish similarly sized particles based on surface charge, and gives consistent Zeta potential results for different bias voltages.

The present inventors have appreciated that this method has the disadvantage that the geometry and zeta potential of the sensing pore must be precisely known, must be invariant during analysis, and able to be modelled. In the example described by Kozak et al. the geometry of the pore is assumed to be perfectly conical, and calculations are based on that assumption. The present inventors have appreciated that in practice pores are typically not conical, and in many cases are not even rotationally symmetrical. In application the method described by Kozak et al. requires that the precise geometry and dimensions of a sensing pore are measured and modelled and that the pore charge is accurately known. This is commercially impractical. Simple application of the conical model described by Kozak et al.

as an approximation is also impractical as this requires that the actual size in nanometres of the pore entry and exit must be known along with the actual pore charge. The present inventors have therefore appreciated that in practice the ability of the model to correctly predict fluid flow under different pressures is very limited.

A final method, described by Arjmandi et al, (Arjmandi et al., "Measuring the electric Charge and Zeta Potential of Nanometer-Sized Objects Using Pyramidal-Shaped Nanopores". *Analytical Chemistry*, 2012. 84:8490-8496) is based on measuring the duration of the translocation of particles through a nanopore as a function of applied voltage.

In addition to the disadvantages described above, further disadvantages of existing methods, as appreciated by the present inventors, include:

1. Methods based purely on electrophoresis may be impractical. For example, samples of particles with a wide spectrum of zeta-potentials, potentially reaching from positive to negative values, may require the application of an external pressure in order to capture the whole spectrum of particle zeta-potentials. In addition, when measuring the charge/zeta-potential of very dilute particle suspensions, methods purely based on electrophoresis become impractical due to low count rates. Further, when measuring particle suspensions with a large proportion of nearly neutral particles in the absence of any applied pressure, the majority of the neutral particles may not translocate the pore, and hence not be measured, skewing the results.
2. Changes in zeta potentials of the pore material are often not considered. For biological samples, in particular in situ biomolecular reactions, particles and/or biomolecules (such as DNA or proteins) might coat the pore. If this were the case, the electroosmotic contribution to particle motion might become important.
3. Existing methods often evaluate the average velocities and electric fields only at the end of the sensing zone.
4. Ignoring electro-osmosis greatly limits the choice of nanopore materials that can be used. Many nanopore materials are more highly charged than typical biological particles.
5. Accurate measurement of the charge of a particle depends largely on the sampling frequency of the electronics.

Embodiments of the invention overcome or at least mitigate at least some of the problems associated with existing methods by providing a method for the measurement of particle surface charge that: enables particle by particle charge measurements; is able to measure a large number of particles; is not limited by requirements of measuring the system geometry at a high precision prior to analysis; includes a consideration of convection and electroosmosis in its theoretical approach; and incorporates a differential pressure across the nanopore that can be used to slow down the translocation of particles, allowing better resolution of the blockade shape for each particle, which is particularly useful for accurate calibration of the nanopore with particles of a known Zeta Potential.

In certain embodiments, the present invention provides a method of using the size and shape of a signal generated by individual objects travelling through a resistive pulse sensor of either known or unknown geometry, for example a nanopore or micropore (or, more generally, an aperture), to measure their relative electrophoretic mobility. The surface charge density and Zeta Potential of each object can be calculated by calibrating the resistive pulse sensor using particles of defined surface charge density or Zeta Potential respectively.

The objects passing through the pore for analysis can consist of any material including solids (e.g. carbon, silica, polymers, metals), biological particles (e.g. viruses, bacteria, microvesicles, exosomes, liposomes, cells), liquids (e.g. emulsions) or gases (e.g. nanobubbles). In the preferred form solid calibration particles (e.g. carboxylated polystyrene) are used. Objects passing through the pore are therefore referred to as "particles" below.

When each particle passes through the pore, there is a resultant resistive pulse or "blockade". For objects with a small aspect ratio (largely spherical), the general shape of any given blockade is determined by the shape of the pore this general shape is "stretched" in magnitude (height) and duration (width) depending on the size and the velocity of each particle.

By working with relative magnitudes for each blockade, the difference in particle size can be eliminated from the charge analysis calculations. When the proportional blockade magnitude is equal for any given particles, those particles are at the same position in the pore (or at least are assumed to be at the same position). The relative velocity of those particles can therefore be directly derived by comparing the time it has taken for the particles to get to that point from any consistent defined point on the blockade pulse.

Particles travelling through a pore with a net pressure and voltage bias will have three velocity components:

1. Convection—the pressure driven flow of fluid will carry particles with it
2. Electrophoresis—the particle charge will cause the particles to move through the surrounding fluid towards the oppositely charged electrode
3. Electro-osmosis—the surface charge of the pore membrane (typically negative) attracts a higher density of oppositely charged (typically positive) ions to be present in the vicinity of the pore. These positive ions move towards the negative electrode and carry water molecules with them to create a "plug flow" of fluid.

Typically, only the electrophoresis component will vary between particles on the basis of surface charge. The present invention provides a method of resolving particle velocity into these three components and deriving the surface charge of an unknown particle by comparing the measured electrophoretic velocity with that of a calibration particle with known surface charge.

For any two particles under the same experimental conditions, the effective particle position within the sensor will be the same when the relative blockade magnitude is the same. Thus for a resistive pulse generated by a particle of unknown surface charge (zeta potential), the measured velocity, along with the known convective and electro-osmotic components derived from calibration particles, are used to calculate electrophoretic velocity of the measured particle. The particle surface charge (zeta potential) is then calculated by comparison of this measured electrophoretic velocity with the calibration particles of known surface charge (zeta potential).

The strength of this novel method is in its simplicity. The method does not require any prior knowledge of the geometry of the sensor, which is prohibitively expensive and time-consuming to measure on a commercial basis (using electron microscopy or similar). The relative electrophoretic velocity of each individual unknown object is simply calibrated against a known particle set based purely on resistive pulse magnitude and shape, with minimal time and processing power required.

This method of charge measurement works best if:
The objects to be measured are suspended in an electrolyte, at a concentration that allows multiple objects to be measured (ideally over a period of a few minutes for operator convenience).
The objects to be measured are smaller than the sensing area to avoid blockages.
Sampling frequency of the current is sufficiently fast to capture a number of data points on each pulse. If sampling frequency is too slow for a particular setup, pulses can be slowed down by application of a pressure differential across the pore or adjustment (even reversal) of the applied bias voltage.
The signal to noise ratio of the pulse is sufficiently large that the reference points of interest can be measured with a good degree of accuracy. If the signal to noise ratio is too small, the signal can be increased by increasing the applied bias voltage and (for flexible pores) reducing the size of the sensor.
Electrophoresis is a significant proportion of the total forces acting on the objects being measured (in particular the calibration particles). This can normally be achieved by increasing bias voltage and reducing pressure differential.

For measurement of real-life samples with a pore, particularly biologically derived samples, there can be a number of complicating factors. These include:
i) Binding of sample particles (or other components of the sample fluid) to the pore based on opposite polarities.
ii) Non-specific binding of sample particles (or other components of the sample fluid) to the pore.

Either of these scenarios is likely to cause a change to the Zeta Potential of the membrane $\xi_m$, which will be expected to directly affect the calculated value of absolute Zeta Potential for each sample particle.

In cases where the pore is coated by charged particles or biomolecules (such as proteins or DNA) the pore zeta potential can change and affect electroosmosis. The pore zeta potential is evaluated in order to accurately measure particle zeta-potentials. Pore zeta potentials can be determined in situ via streaming potential measurements using variable external pressure applied to the pore. The movement of a liquid through a pore, by applying some variable external pressure creates a streaming potential and streaming current. The pore zetapotential is calculated from the streaming potential vs pressure slope, taking into account the geometry of the pore.

This in situ measurement of the pore zeta potential is useful when chemical and/or biological reactions are monitored in resistive pulse sensors. Different biological systems can affect the pore in very different ways, and checking the Zeta potential of the pore both before and after measuring a biological sample allows these changes to be detected and quantified.

Another approach to compensate for this binding effect is through the addition of calibration particles (of known Zeta Potential) to the sample fluid, which will then be measured under identical conditions to the sample. This method can provide an absolute surface charge measurement even if the Zeta Potential of the pore has been modified by, for example, exosomes, liposomes, proteins, aptamers, DNA, RNA or any other agents. An advantage of this approach is that if the pore characteristics change during, and/or as a result of, the analysis the calibration particles can be used to account for the change through the course of the analysis and provide correct sample measurements. This method can be enhanced through the addition of multiple calibration particle sets each of different known Zeta potentials.

A further approach to treating problems associated with the binding effects is to prevent binding through surface treatment of the pore. This can consist of permanently coating the pore surface with an anti-fouling agent. Alternatively the treatment can involve adding a "blocking agent" to the pore just prior to measurements, which binds to all of the available attachment sites on the surface of the pore and gives a known stable Zeta Potential for the duration of the calibration and sample measurements. An advantage of using a blocking agent is that the blocking agent can be matched to accommodate different sample particle types and carrier fluids.

Aspects of the present invention are set out in the claims.

DETAILED DESCRIPTION OF CERTAIN EMBODIMENTS OF THE INVENTION

Figure 1:
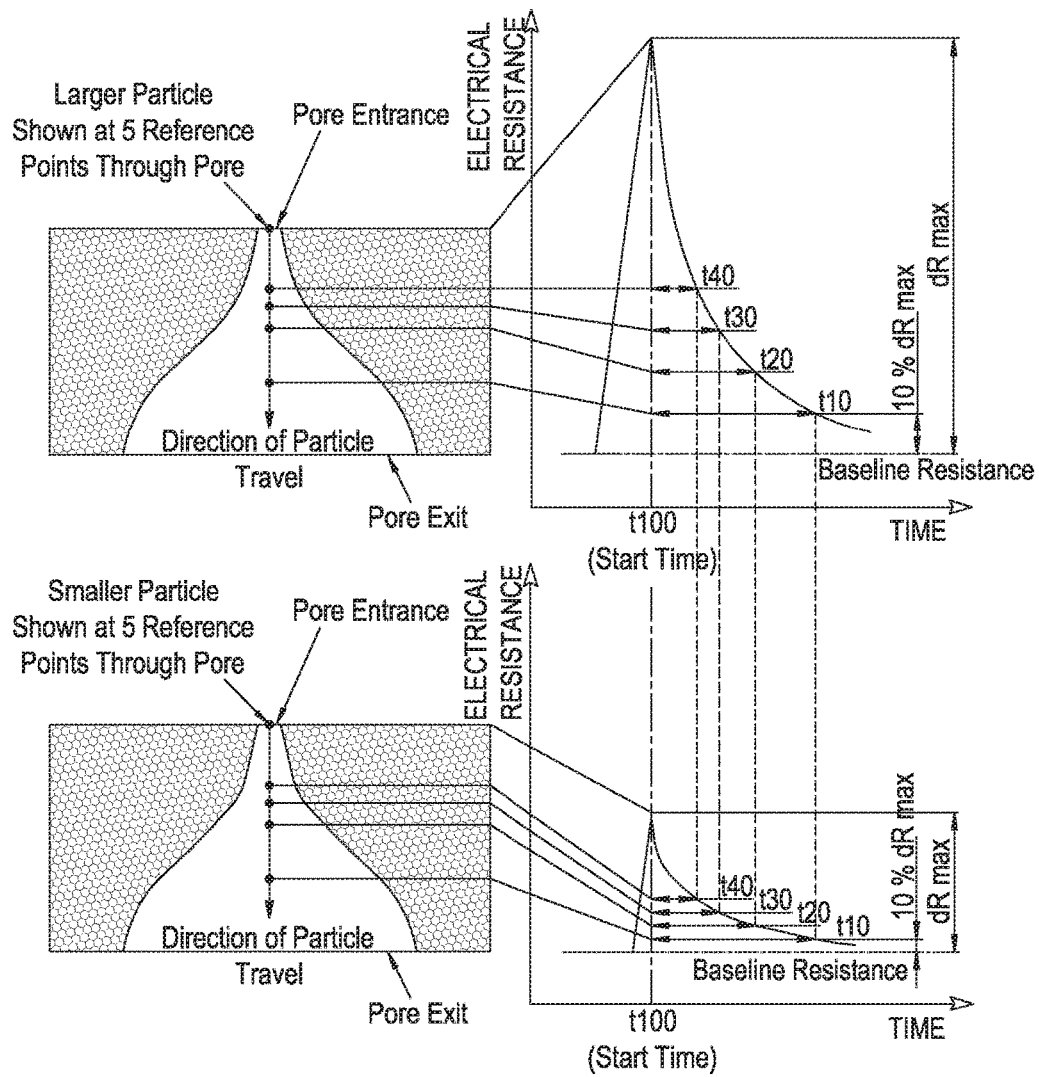
FIG. 1 is a schematic comparison of the blockade shapes resulting from a larger and smaller particle travelling at the same speed, for a generally conical aperture.

Certain embodiments of the invention involve the use of the apparatus disclosed in WO2013017671, the entire contents of which are hereby incorporated by reference.

In certain embodiments of the invention, use is made of a nanopore or micropore of fixed or variable geometry, formed in an impermeable membrane. The exact geometry and dimensions of this pore may be known but typically the exact geometry and dimensions of the pore would be unknown.

The membrane is fitted into apparatus which allows a well (or reservoir or chamber) of electrolyte to be placed on either side of the membrane—the wells are connected to each other only through the pore itself. In one form, the aperture or pore may be provided as a (small) hole in a sheet, the sheet forming (part of) a wall between the two chambers and thereby separating the chambers from each other. The apparatus contains at least one electrode in contact with each of the electrolyte wells such that a user defined bias voltage can be applied across the pore and the resulting electric current through the pore can be monitored. In certain embodiments of the invention a user defined electric current may instead be applied through the pore and the resulting voltage across the pore may be monitored.

The apparatus includes a means to vary the pressure applied to either one or both of the electrolyte wells such that a user defined differential pressure (Pap) can be applied in either direction across the pore, resulting in a convective flow of electrolyte from one well to the other or vice versa.

The inherent pressure head of the system (Pin) due to gravitational forces and/or surface tension is known and consistent from measurement to measurement (typically achieved by using the same volume of fluid).

The objects passing through the pore for analysis can consist of any material including solids (e.g. carbon, silica, polymers, metals), biological particles (e.g. viruses, bacteria, microvesicles, liposomes, cells), liquids (e.g. emulsions) or gases (e.g. nanobubbles). In the preferred form solid calibration particles (e.g. carboxylated polystyrene) are used. Objects passing through the pore are therefore referred to as "particles" below.

The method allows for quantitative measurement of chemical/biochemical reactions on particle surfaces that alter particle zeta potential. The capacity to detect such changes in particle zeta potential forms the basis of pore based diagnostic assays. Surface reactions may include the specific binding of aptamers, proteins, antibodies, lectins, DNA, RNA, other chemical or biochemical reagents to the surface of the particle. The particle may include cells, extracellular vesicles, subcellular complexes, liposomes, synthetic particles, but not limited to these. The reaction may be quantified by comparative measurement of particle zeta potential before and after incubation of the particle with the surface modifier for a period of time under appropriate conditions or the reaction process may be monitored continuously in real time.

When each particle passes through the pore, there is a resultant resistive pulse or "blockade". For objects with a small aspect ratio (largely spherical), the general shape of any given blockade is determined by the shape of the pore; this general shape is "stretched" in magnitude (height) and duration (width) depending on the size and the speed of each particle.

FIG. 1 illustrates the passage of a larger particle (top half of FIG. 1) and a smaller particle (bottom half of FIG. 1) travelling through a pore at the same speed, with corresponding plots of electrical resistance against time showing the resulting blockade shapes.

The method identifies the point of greatest resistance in the signal trace (the blockade peak), which in the preferred pore setup is close to the beginning of the blockade. For each blockade, the time at which the peak occurs is defined as $t_{100}$ (time at 100% of peak magnitude) and the maximum magnitude of the pulse (relative to the local baseline resistance) is recorded as dR max.

In the simplest embodiment, the blockade is divided into "n" sections, and the duration from $t_{100}$ is recorded for each section. In the example shown in FIG. 1 there are n=4 sections: 40%, 30%, 20% and 10% of dR max. The duration from $t_{100}$ to each of these sections is defined at $t_{40}$, $t_{30}$, $t_{20}$ and $t_{10}$.

By working with relative magnitudes for each blockade, the difference in particle size can be eliminated from the charge analysis calculations. When the proportional blockade magnitude is equal for any given particles, those particles are at the same position in the pore. The relative velocity of those particles can therefore be directly derived by comparing the time it has taken for the particles to get to that point from $t_{100}$.

Particles travelling through a pore with a net pressure and voltage bias will have three velocity components:
1. Convection—the pressure driven flow of fluid will carry particles with it
2. Electrophoresis—the particle charge will cause the particles to move through the surrounding fluid towards the oppositely charged electrode
3. Electro-osmosis—the surface charge of the pore membrane (typically negative) attracts a higher density of oppositely charged (typically positive) ions to be present in the vicinity of the pore. These positive ions move towards the negative electrode and carry water molecules with them to create a "plug flow" of fluid.

The magnitude of the convection component increases linearly with applied pressure, and the magnitudes of the electrical components increase linearly with applied voltage.

Combining the Electrical Forces

Electrophoresis and electro-osmosis are opposing forces if the particle charge (Zeta Potential "$\xi_p$") has the same polarity as the membrane charge (Zeta Potential "$\xi_m$"). Their relative velocity components per mV of Zeta Potential are equal and opposite, so if the Zeta Potential of both the particle and the pore are known (as is the case when using calibration particles), the velocity components can be simplified to two:
1. Convection velocity or "$v_c$"
2. Electrical velocity or "$v_e$" obtained by setting the effective Zeta Potential of the pore to zero and setting the net Zeta Potential of the particle as follows:

$$\xi_{net} = \xi_p - \xi_m \quad \text{Equation A:}$$

The relative velocity "$(v^i_x)_{tot}$" for a particle i at any given point in space x within the pore (reached after time $T^i_x$) is given by:

$$(v^i_x)_{tot} = \frac{x}{T^i_x} = \frac{\int_0^{T^i_x} v^i(t)\, dt}{T^i_x}. \quad \text{Equation B}$$

Please note that x is set equal to 0 at the pore entrance. $v_{tot}$ is the sum of the time averaged electrical and convection velocity components (Equation C). Electrical and convection time averaged velocities are calculated in a similar way as $v_{tot}$ in equation B, by substituting $v_{tot}$ with $v_e$ or $v_c$. Time averaged velocities are related with inverted times through Equation B.

$$(v^i_x)_{tot} = (v^i_x)_e + (v^i_x)_c \quad \text{Equation C:}$$

It should be noted that this equation can be applied at any given reference point x in the pore—for the simple worked example the surface charge of the particle is calculated at each of the four reference points $t_{40}$, $t_{30}$, $t_{20}$, and $t_{10}$ and the answers are averaged. More advanced analysis methods can be applied to improve the data quality, as detailed below.

The inverse times $1/T^i_x$ are averaged over N calibration particles (typically 200), as shown in Equation D.

$$\frac{1}{Tx} = \sum_{i=1}^{N} \frac{1}{T^i_x} \Big/ N \quad \text{Equation D}$$

In the same way $(v^i_x)_{tot}$ are averaged over N calibration particles:

$$(v_x)_{tot} = \Sigma_{i=1}^{N}(v_x^i)_{tot}/N \qquad \text{Equation E:}$$

$(v^i_x)_{tot}$ is proportional to $1/T^i_x$ (Equation B). For the purpose of the calculation and from here on $(v^i_x)_{tot}$ is set equal to $1/T^i_x$, with $T^i_x$ being the duration the particle i takes, from entering the pore to the position x within the pore.

Equation E also applies for $v_e$ and $v_v$ and hence Equation F applies:

$$(v_x)_{tot} = (v_x)_e + (v_x)_c \qquad \text{Equation F:}$$

Calibrating the Pore and Quantifying the Convection Component

Quantifying the convection component $v_c$ in Equation F will leave an electrical component $v_e$, that can be used to calculate the surface charge density and zeta potential of the particle.

Charged calibration particles of closely controlled diameter and known Zeta Potential $\xi_p$ are typically used to calibrate the pore. A number of calibration particles (typically more than 200 per analysis) are analysed in the pore at a number of applied voltages V (e.g. V=0.3 V, 0.5 V and 0.7 V), and the average $(v_x)_{tot}$ is calculated by averaging $(v^i_x)_{tot}$ over. N particles (see Equation E).

The change in $(v_x)_{tot}$ with voltage is entirely due to the $(v_x)_e$ term, since the pressure is unchanged between the three measurements.

$(v_x)_c$ can be calculated in several ways:

Method 1: $(v_x)_{tot}$ is plotted against voltage and the defined line is extrapolated back to V=0, at which point there is no electrical force on the particles and hence no electrical velocity contribution $((v_x)_e=$so $(v_x)_c=(v_x)_{tot}$.

Method 2: $(v_x)_c$ of the calibration is determined by measuring the calibration at various pressures and plotting $(v_x)_{tot}$ vs pressure. The slope of the $(v_x)_{tot}$ vs P linear curve is proportional to the relative convective velocity per unit pressure $v_x^P$ which is defined as:

$$v_x^P = (v_x)_c(P_{in} + P_{ap}) \qquad \text{Equation G:}$$

$P_{in}$ is the inherent pressure head (a known constant for any given equipment setup) and $P_{ap}$ the applied pressure.

$v_x^P$ can be used to calculate the convection velocity $(v_x)_c$ at any pressure or vacuum setting $P_{ap}$. $(v_x)_c$ and $(v_x)_e$ can be either determined together (by calculating one and subtracting that from (Vx)tot to determine the other) or calculated independently by application of a number of pressures and voltages (by plotting $1/T^i_x$ vs P and $1/T^i_x$ vs V, respectively). The latter method may give better measurement repeatability when sample and calibration particles are analysed over a wide range of pressures and voltages. In particular, by calculating the two components separately it is possible to more accurately assess the velocity component when it is dominant, and similarly with the electrical component. When one component is dominant the value calculated for the other component may be less accurate. If the settings (voltage and pressure) are adjusted to make one force (convection or electrical force) dominant over the other, then it is possible to calculate that force and corresponding velocity component more accurately. The settings can then be adjusted to make the other force dominant, to more accurately calculate that other force and corresponding velocity component. This method may avoid the magnification of measurement errors of the non-dominant component as the relative contribution of the forces varies. For example, the convection velocity component may make up only a small fraction of the total velocity at the voltage sweep calibration settings, so large errors may be present in the calculated convective velocity per unit pressure. When a large pressure or vacuum is applied that error may be greatly magnified. Therefore, measurements may be taken at a second pressure value, and the flow per unit pressure can thus be calculated independently. This may result in a small discrepancy at the voltage sweep calibration point, but gives improved stability for applying a range of pressures and vacuums.

Quantifying the Electrical Component for the Calibration Particles

Knowing the average $(v_x)_{tot}$ and average $(v_x)_c$, average $(v_x)_e$ can now be calculated for the calibration particles (Equation F), using the measurements taken at any of the non-zero voltages V. The relative electrical velocity per unit voltage $v_x^V$ can be calculated as follows:

$$v_x^V = \frac{(v_x)_e}{V} \qquad \text{Equation H}$$

$v_x^V$ can be used to calculate the theoretical $(v_x)_{e\ Cal}$ of the calibration particles' at any voltage V.

Calculating Zeta Potential of Sample Particles

Particles with the same Zeta Potential have the same surface charge density (assuming that the Smoluchovski approximation applies which for particles of interest in physiological buffers is typically the case), and particles with the same surface charge density have the same electrophoretic mobility under an applied voltage, independent of particle diameter.

The Zeta Potential of each sample (unknown) particle is calculated as follows:

Calibration particles are cleaned out of the pore and fluid wells and sample particles are analysed in the same electrolyte at the same pore stretch (for a flexible pore). Applied pressure and voltage may differ from the calibration run.

The convection velocity $(v_x)_{c\ Sample}$ for the sample particle measurement pressure is the product of $v_x^P$ and the net pressure $(P_{in} - P_{ap})_{Sample}$—(Equation G).

The electrical velocity of the sample, particle i $(v^i_x)_{e\ Sample}$ is the measured $(v^i_x)_{tot\ Sample}$ minus the calculated $(v^i_x)_{c\ Sample}$ (Equation F).

The theoretical electrical velocity of the calibration particles $(v_x)_{e\ Cal}$ is calculated at the sample $V_{Sample}$ setting (Equation H) and the two velocities are compared as follows:

$$\frac{(v_x^i)_{e\ Sample}}{(v_x)_{e\ cal}} = \frac{\xi^i_{x\ net\ Sample}}{\xi_{net\ Cal}} \qquad \text{Equation I}$$

$\xi_{net\ Sample}$ can be calculated because the three other terms are known. The Zeta Potential of each sample particle can now be calculated using equation A:

$$\xi_{p\ Sample} = \xi_{net\ Sample} + \xi_m \qquad \text{Equation J:}$$

The zeta potential of each sample particle i can be calculated from the ratio of the electrical velocities of sample and calibration (Equation I). The zeta potential of each sample particle i is given by averaging respective zeta potential values, calculated at positions x.

$$\xi_{Sample}^i = \frac{\sum_x \xi_{x,Sample}^i}{\sum_x}$$ Equation K $$= \frac{\sum_x \left((v_x^i)_{Sample} - v_x^P * (P_{in} + P_{ap})_{Sample}\right) / ((v_x^V)_{Cal} * V_{Sample})}{\sum_x} *$$

$$\xi_{net\ Cal} + \xi_m$$

Maximising Information Content from the Data

The simplest embodiment of the method analyses predefined points on each blockade (40% to 10% of the blockade peak magnitude dR max in the example above).

In reality the data stream is neither pure nor continuous. Depending on a number of factors including the nanopore size and shape, the applied pressure, the sampling frequency of the electronics and the signal to noise ratio of the blockades, certain sections of each analysed blockade will contain more information than others.

Referring to the blockade shape in FIG. 1, the accuracy of information extracted from each blockade depends primarily on the accuracy of:
1. Identifying the blockade maximum dR max (or a distinct datum feature for alternative pore geometries see FIG. 2)
2. Identifying the time of dR max (t100 or another distinct datum feature FIG. 2)
3. Identifying t40, t30, t20, t10 (or other distinct features on the blockade FIG. 2)

A particle travelling very fast will move a long way between data sampling points. It is therefore likely that the very peak of the blockade Will fall between sample points and will not be correctly identified, leading to an error in the value of both dR max and t100. An error in t100 will generate a large percentage error in the calculated t90, for example, but a much smaller percentage error in t10 —so the trailing end of the blockade may give better quality information than the area around the peak.

A particle travelling slowly will not move a long way between data sampling points, so the identified blockade peak dR max and time t100 are likely to be relatively accurate. In this case, better information may be obtained at t90 than at t10, due to the (9x) higher signal to noise ratio around the blockade peak. When noise is a high percentage of the measured signal, the calculated time to reach the designated blockade height (e.g. t10) becomes less accurate.

Information quality can be improved in a number of ways, including but not limited to the following:
1. Adjust the applied pressure and voltage to optimise the blockade profiles for each sample. This could either be done by feedback to the user to make system adjustments, or fully automated. An optimised system would aim for blockades with a number of sample points around the peak area, but even the least charged particle must still travel through the pore in the same direction as the calibration particles.
2. There will be variation in size and surface charge within the sample even when the system settings have been optimised, so optimising the information extracted from faster and smaller blockades is still critical:
   a. Using the known profile of the blockade from the calibration particle measurements and extrapolating from points further down the blockade, the peak dR max and the time t100 for each sample blockade can be calculated more accurately
   b. Using similar extrapolation at the tailing end of the blockade will reduce the impact of noise on the measured resistance.
3. Identify the section of each blockade that will give optimum information quality by calculating the timing errors and noise errors across the whole blockade.
4. Implement signal to noise improvements by, for example:
   a. Modifying the system electronics to allow application of a larger voltage for a given pore size.
   b. Implement algorithms that allow signal information to be extracted from within the noise floor. Such algorithms are well known in the art.

Application of the Method to Alternative Geometries

The principles of the method can be applied to pores of any geometry, by identifying one or more distinct features in the blockade profile that allow the relative velocities of different particles to be calculated. The example in FIG. 2 shows a pore with a different profile.

Figure 2:
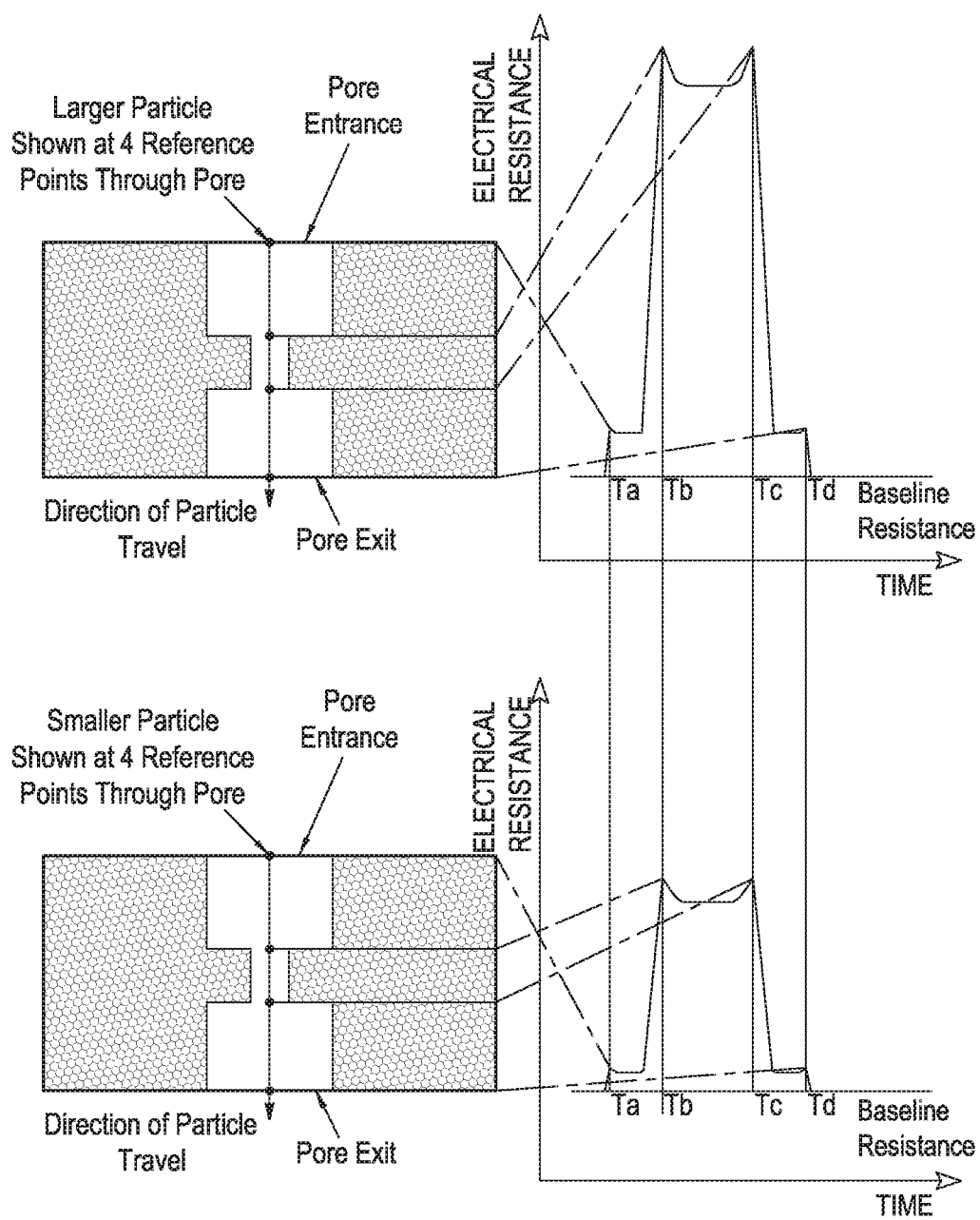
FIG. 2 is a schematic comparison of the blockade shapes resulting from a larger and smaller particle travelling at the same speed, for a different aperture shape.

With the pore shape in FIG. 2 there are four distinct features that could be used to calculate relative times Tn. For example, the time difference between the two maxima could be used:

$$Tn = Tc - Tb$$ Equation M:

EXAMPLE 1

Figure 3:
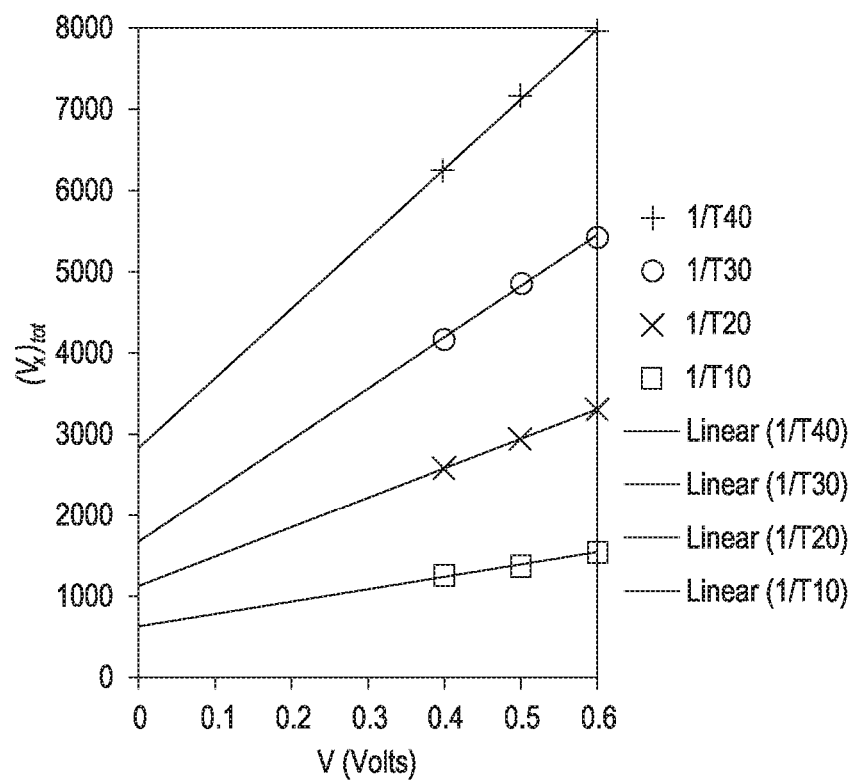
FIG. 3 is a plot of Average (Vx)tot (i.e., 1/Tx) against bias voltage V for calibration particles (Example 1).
Figure 4:
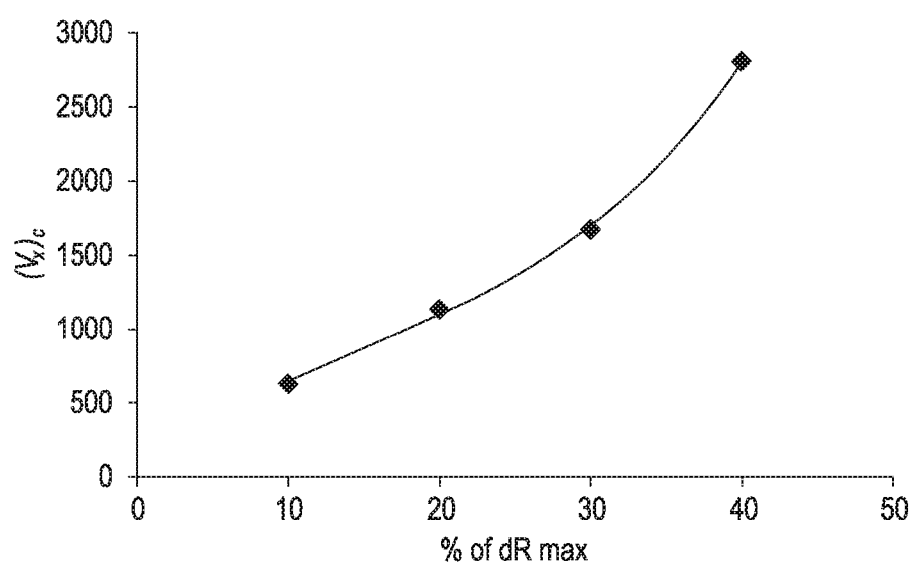
FIG. 4 is a plot of Calculated (Vx)c as a function of % of dR max for calibration particles, from 10% to 40% of dR max (Example 1).

This example shows the use of calibration particles to establish $v_x^P$ and $v_x^e$. Measurements of the calibration particles were made at three different applied voltages; 0.4V, 0.5V, and 0.6V. The results are displayed in FIG. 3 and FIG. 4. The measurement details are:

Nanopore—Izon NP200
  Carboxylated polystyrene calibration particles CPC200
    —Izon Tris Buffer 0.1 M KCl
  Applied Voltages (V): 0.4 V, 0.5 V and 0.6 V
  Applied Pressure (Pap): 0 mm $H_2O$
  Inherent Pressure (Pin): 4.7 mm $H_2O$
  Particle Count—369 at V=0.4 V, 619 at V=0.5 V, 596 at V=0.6 V
  At V=0 V there are no electrical forces so $(v_x)_{tot} = (v_x)_c$:
  $(v_x)_{c\ 40} = 2806\ s^{-1}$ and $v_x^P{}_{40} = (2806/4.7) = 597\ s^{-1}$
  $(v_x)_{c\ 30} = 1672\ s^{-1}$ and $v_x^P{}_{30} = (1672/4.7) = 356\ s^{-1}$
  $(v_x)_{c\ 20} = 1131\ s^{-1}$ add $v_x^P{}_{20} = (1131/4.7) = 241\ s^{-1}$
  $(v_x)_{c\ 10} = 626\ s^{-1}$ and $v_x^P{}_{10} = (626/4.7) = 84\ s^{-1}$ $(v_x)_c$ for the calibration particles can be calculated at any of the applied voltages, for example $(v_x)_{c\ 40}$ is calculated below at all three voltages:

| V (V) | $(v_x)_{tot\ 40}$ $(s^{-1})$ | $(v_x)_{c\ 40}$ $(s^{-1})$ | $(v_x)_{e\ 40}$ $(s^{-1})$ = $(v_x)_{tot\ 40} - (v_x)_{c\ 40}$ | $v_x^e{}_{40}$ $(s^{-1})$ = $(v_x)_{e\ 40}/V$ |
|---|---|---|---|---|
| 0.4 | 6224 | 2806 | 3418 | 8454 |
| 0.5 | 7166 | 2806 | 4360 | 8720 |
| 0.6 | 7946 | 2806 | 5140 | 8567 |
|  |  |  | Average: | 8580 |

EXAMPLE 2

Figure 5:
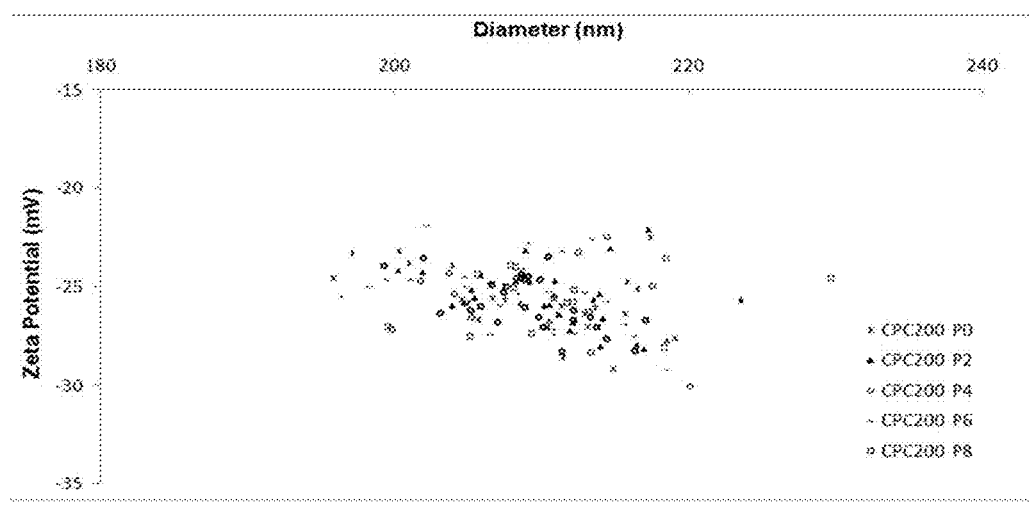
FIG. 5 is a plot of zeta potential vs size for multiple applied pressures, showing repeatable results.

This example demonstrates measuring the sample at multiple pressures. This illustrates the fact that system pressure can be varied without having any material effect on the analysis result as can be seen in FIG. 5. The Measurement details are:

Calibration (and Sample) Particles—carboxylated polystyrene "CPC200"
Nanopore—Izon NP200
Electrolyte Izon Tris Buffer 0.1 M KCl
Applied Voltage (V): 0.8 V
Applied Pressure (Pap): 0 mm $H_2O$ to 8 mm $H_2O$ in steps of 2 mm ("P0" to "P8")
Inherent Pressure (Pin): 4.7 mm $H_2O$
System calibrated with ZERO applied pressure It can be seen from FIG. 5 that the measured mean Zeta potential does not change significantly with applied pressure. This result is obtained using $v_x^P$ against calibration particles measured at zero applied pressure. Pulse height is slightly truncated as applied pressure increases, leading to a reduced mean diameter value.

EXAMPLE 3

Figure 6:
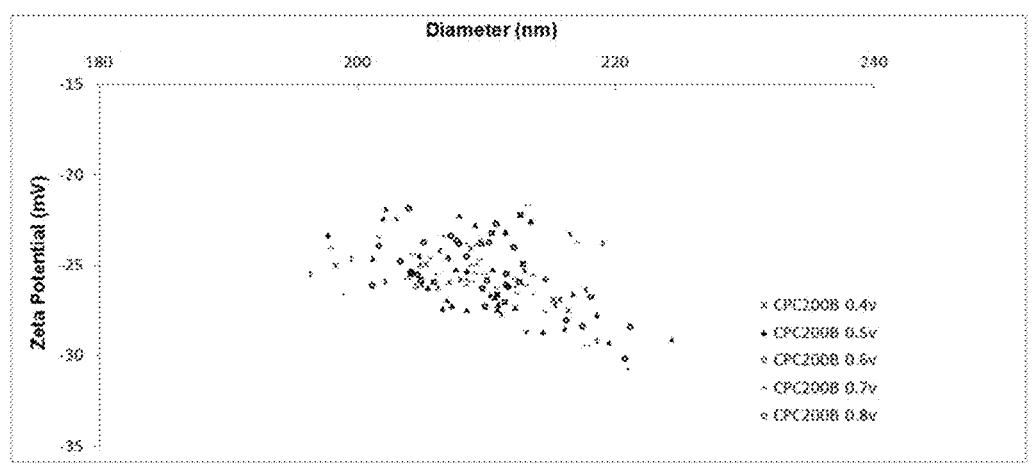
FIG. 6 is a plot of zeta potential vs size for multiple applied bias voltages, showing repeatable results.

This example demonstrates measuring the sample at multiple bias voltages. This illustrates the fact that applied bias can be varied without having any material effect on the analysis result as can be seen in FIG. 6. The Measurement details are:

Calibration (and Sample) Particles—carboxylated polystyrene "CPC200"
Nanopore—Izon "NP200"
Electrolyte—Izon Tris Buffer 0.1 M KCl
Applied Pressure (Pap): 0 mm $H_2O$
Inherent Pressure (Pin): 4.7 mm $H_2O$
Applied Voltage (V): 0.8 V for calibration
System calibrated with ZERO applied pressure It can be seen from FIG. 6 that the measured mean Zeta potential does not change significantly with applied voltage. This result is obtained using $v_x^e$ against calibration particles measured at 0.8 V and zero applied pressure.

EXAMPLE 4

Figure 7:
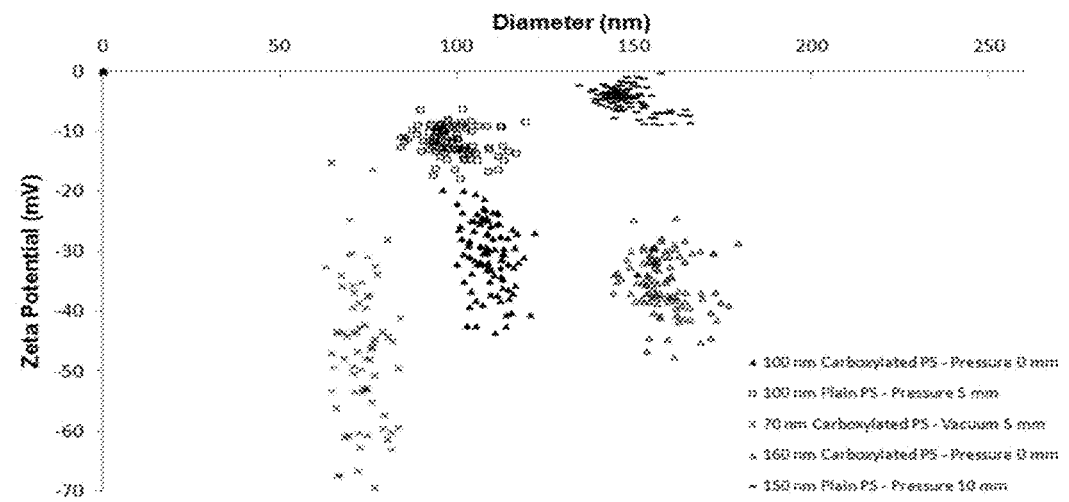
FIG. 7 is a plot of zeta potential vs size for highly charged (Carboxylated) and less charged (Plain) PS particles.

This example demonstrates measuring charged and uncharged particles of different diameter. The measurement details are:

Calibration Particles—carboxylated polystyrene, mean diameter 118 nm
Nanopore—Izon "NP100"
Electrolyte—PBS 0.25 M
Applied Pressure (Pap): 0 mm $H_2O$ calibration
Inherent Pressure (Pin): 4.7 mm $H_2O$
Applied Voltage (V): 0.66 V—calibration and sample It can be seen from FIG. 7 that the plain NIST traceable polystyrene particles (CPN100 and CPN150) are clearly distinguished from the carboxylated polystyrene CPC70, Bangs 6569 and CPC100 particles.

EXAMPLE 5

Figure 8:
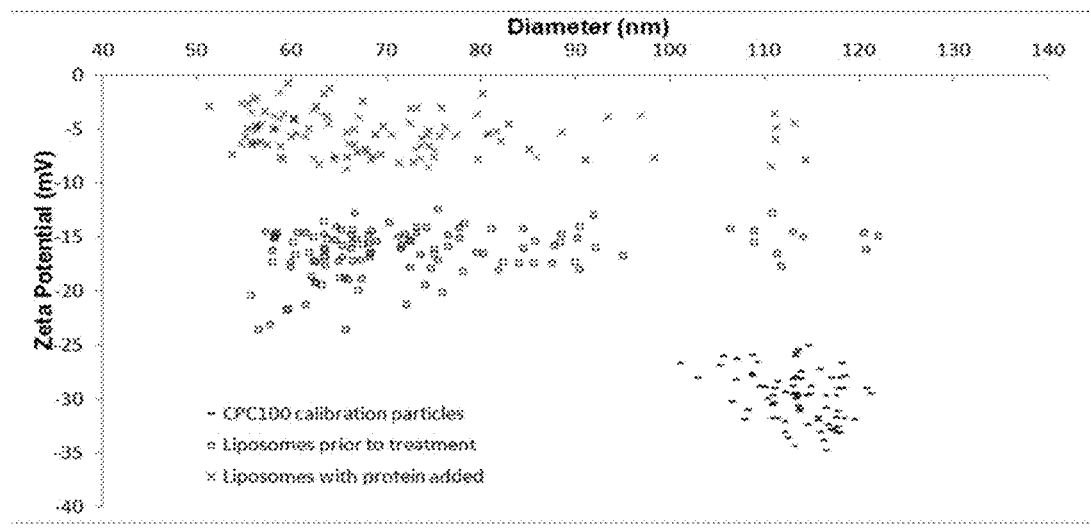
FIG. 8 is a plot of zeta potential vs size illustrating the detection of the surface modification of liposomes via detection of a change in zeta potential.

This example demonstrates the measurement of particle zeta potential after deliberate surface modification to demonstrate detection of specific surface targets. This example shows the binding of a protein (CD63) to a liposome that was modified to bind CD63. FIG. 8 shows the liposomes before and after binding of CD63. A shift in zeta potential toward a more positive value is observed upon binding of protein, which was expected as the protein is slightly positively charged in experimental conditions. In FIG. 8, it can be seen that the liposomes before protein binding form a distinct group from the liposomes with surface-bound protein. This illustrates analyses that can be used to detect particular targets in the sample. FIG. 8 also shows a control particle set of known, negative charge, which validates the results.

EXAMPLE 6

Figure 9:
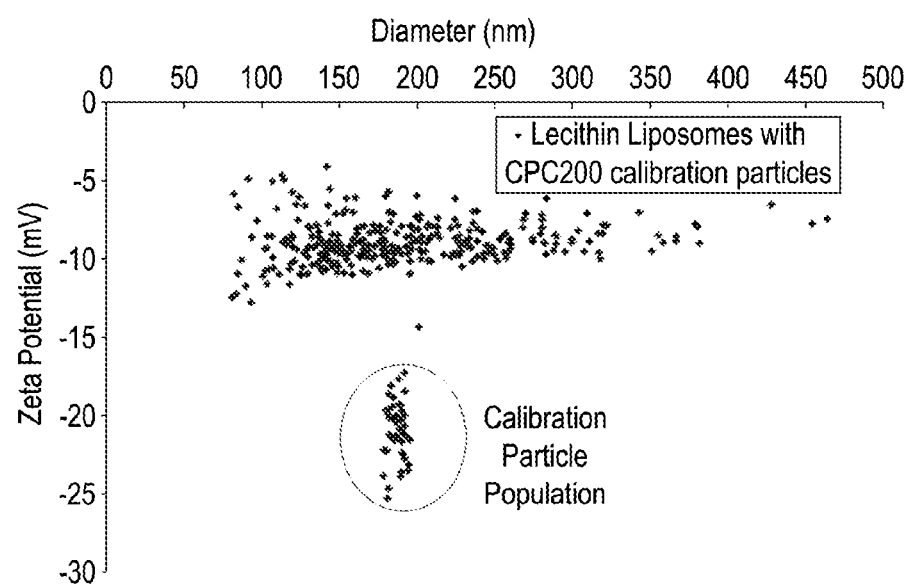
FIG. 9 is a plot of zeta potential vs size illustrating the measurement of a suspension of liposomes "spiked" with carboxylated calibration particles.

This example demonstrates running an analysis whereby calibration particles (of a known Zeta Potential) are added to the sample fluid. FIG. 9 shows the measurement of lecithin liposomes with calibration particles added as a sample spike run within the sample set. The two similarly sized particle sets (Liposomes and calibration particles) can be clearly distinguished based on their surface charge, and the accuracy of the data can be benchmarked by the Zeta Potential result for the calibration particles (which have a known average Zeta Potential of −20 mV in this electrolyte).

General Remarks

As set out in the present specification, according to embodiments of the present invention a number of values (such as pressure, time, voltage, current etc.) are measured, determined, calculated or otherwise derived, as well as processed, plotted, stored or otherwise used. It will be understood that, where appropriate (and whether or not specifically mentioned) a reference to such "values" may include a reference to values derived therefrom.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A method of determining a charge of at least one test particle, comprising:
    applying one of an electric current or a voltage across an aperture connecting two chambers, whereby the chambers are at least partially filled with an electrolyte and whereby the at least one test particle is suspended in the electrolyte of at least one of the chambers, wherein the aperture has a geometry that does not need to be known;
    measuring a value indicative of the other of the electric current or the voltage across the aperture;
    determining a time interval between a first and a second point in time, the second point in time corresponding to a point in time when the measured current or the measured voltage has reached a specific proportion of the measured current or the measured voltage at the first point in time; and
    determining the charge of the at least one test particle by:
        determining a value indicative of an electrical velocity component of a total velocity of at least one calibration particle having a known charge, taking into account that the total velocity of the at least one calibration particle comprises a non-zero convective velocity component and the electrical velocity component;
        determining a value indicative of an electrical velocity component of a total velocity of the at least one test particle, taking into account that the total velocity of the at least one test particle comprises a non-zero convective velocity component and the electrical velocity component; and using the determined values indicative of the electrical velocity components of the at least one test particle and the at least one calibration particle to calibrate a quantitative relationship between the charge of the at least one test particle and the determined time interval.

2. The method of claim 1, wherein determining the value indicative of the electrical velocity component of the total velocity of the at least one calibration particle comprises determining a value indicative of the total velocity of the at least one calibration particle and a value indicative of the non-zero convective velocity component of the at least one calibration particle, and subtracting the value indicative of the non-zero convective velocity component from the value indicative of the total velocity.

3. The method of claim 2, further comprising determining a further time interval for the at least one calibration particle, wherein the further time interval is a time interval between a third and a fourth point in time, the fourth point in time corresponding to a point in time when the measured current or the measured voltage for the at least one calibration particle has reached a specific proportion of the measured current or the measured voltage at the third point in time.

4. The method of claim 3, wherein determining the value indicative of the electrical velocity component of the total velocity of the at least one calibration particle comprises determining a respective further time interval at each of a plurality of applied voltages.

5. The method of claim 4, further comprising determining the value indicative of the electrical velocity component of the at least one calibration particle based on:
the plurality of applied voltages, and
the respective further time intervals, or values derived therefrom, at each of the plurality of applied voltages.

6. The method of claim 4, further comprising determining the slope of a curve fitted to a plot of the inverse of the respective further time intervals against the plurality of applied voltages, said slope being indicative of the electrical velocity component per unit voltage for the at least one calibration particle.

7. The method of claim 3, wherein determining the value indicative of the non-zero convective velocity component of the at least one calibration particle comprises measuring a respective further time interval at each of a plurality of applied voltages.

8. The method of claim 7, wherein determining the value indicative of the non-zero convective velocity component of the at least one calibration particle comprises using an extrapolation based on:
the plurality of applied voltages, and
the respective further time intervals, or values derived therefrom, at each of the plurality of applied voltages.

9. The method of claim 7, wherein determining the value indicative of the non-zero convective velocity component of the at least one calibration particle comprises plotting the inverse of the further time intervals against the plurality of applied voltages, and extrapolating a line defined by the plot to a point where the voltage is zero.

10. The method of claim 3, wherein determining the value indicative of the non-zero convective velocity component of the at least one calibration particle comprises measuring a respective further time interval at each of a plurality of applied pressure values, wherein the applied pressure is a pressure that is externally applied to at least one of the two chambers to change or establish a pressure differential across the aperture.

11. The method of claim 10, further comprising:
determining, for the at least one calibration particle, a value indicative of a convective velocity per unit pressure based on the applied pressure values; and
determining the value indicative of the non-zero convective velocity component of the at least one calibration particle based on the value indicative of the convective velocity per unit pressure, the applied pressure, and an inherent pressure head, wherein the inherent pressure head is a contribution to the pressure differential across the aperture that results from a difference in height between the electrolyte in the two chambers.

12. The method of claim 11, wherein determining the value indicative of the non-zero convective velocity component of the at least one calibration particle further comprises:
plotting the inverse of the respective further time intervals against the plurality of applied pressures;
determining the slope of said plot, said slope being indicative of the convective velocity per unit pressure; and
determining the value indicative of the non-zero convective velocity component as the product of the convective velocity per unit pressure and the sum of the applied pressure and the inherent pressure head.

13. The method of claim 2, further comprising determining the charge of the at least one test particle by:
determining a value indicative of the total velocity of the at least one test particle using the value indicative of the total velocity of the at least one calibration particle and the determined time interval for the at least one test particle;
determining a value indicative of the non-zero convective velocity component of the at least one test particle as the product of a convective velocity per unit pressure and the sum of an applied pressure and an inherent pressure head;
determining the value indicative of the electrical velocity component of the at least one test particle by subtracting the value indicative of the non-zero convective velocity component of the at least one test particle from the value indicative of the total velocity of the at least one test particle;
determining a zeta potential of the at least one test particle using the value indicative of the electrical velocity component of the at least one calibration particle, the value indicative of the electrical velocity component of the at least one test particle, a zeta potential of the aperture, and a zeta potential of the at least one calibration particle, wherein the zeta potential of the at least one calibration particle is determined using the known charge of the at least one calibration particle; and
determining the charge of the at least one test particle using the determined zeta potential of the at least one test particle.

14. The method of claim 13, further comprising determining the charge of the at least one test particle by averaging a plurality of zeta potential values determined for a plurality of specific proportions.

15. The method of claim 1, wherein the value indicative of the electrical velocity component and the non-zero value indicative of the non-zero convective velocity component of the total velocity of the at least one calibration particle are determined independent of each other.

16. The method of claim 1, wherein the specific proportion is set based on an average total velocity of the at least one test particle relative to a data sampling rate.

17. The method of claim 16, wherein:
when the average total velocity of the at least one test particle is greater than a predetermined threshold, the specific proportion is set to a first value; and
when the average total velocity of the at least one test particle is less than the predetermined threshold, the specific proportion is set to a second value;
wherein the first value is smaller than the second value.

18. The method of claim 1, wherein the at least one test particle and the at least one calibration particle are suspended in the same electrolyte and are analyze in the same experiment, or wherein the at least one test particle is a biological particle, the method further comprising determining a zeta potential of the aperture before and after measurement of the at least one test particle.

19. The method of claim 1, wherein the total velocity of the at least one calibration particle is a sum of the non-zero convective velocity component and the electrical velocity component.

20. The method of claim 1, wherein the total velocity of the at least one test particle is a sum of the non-zero convective velocity component and the electrical velocity component.

* * * * *